United States Patent [19]

Yates

[11] Patent Number: 5,087,778

[45] Date of Patent: * Feb. 11, 1992

[54] REGENERATION OF ZEOLITES USED FOR PURIFYING 1,1,1,2-TETRAFLUOROETHANE

[75] Inventor: Stephen F. Yates, Arlington Heights, Ill.

[73] Assignee: Allied-Signal Inc., Morris Township, Morris County, N.J.

[*] Notice: The portion of the term of this patent subsequent to Mar. 6, 2007 has been disclaimed.

[21] Appl. No.: 506,969

[22] Filed: Apr. 10, 1990

[51] Int. Cl.$^5$ .......................... C07C 17/39; B01J 20/34
[52] U.S. Cl. ...................................... 570/179; 502/34; 502/36; 502/38; 502/39
[58] Field of Search ...................... 502/34, 38, 36, 39; 570/179

[56] References Cited

U.S. PATENT DOCUMENTS

| | | | |
|---|---|---|---|
| 4,906,796 | 3/1990 | Yates | 570/179 |
| 4,940,824 | 7/1990 | Yates | 570/179 |
| 4,940,825 | 7/1990 | Yates | 570/179 |

*Primary Examiner*—Alan Siegel
*Attorney, Agent, or Firm*—Harold N. Wells; Jay P. Friedenson; Gerard P. Rooney

[57] ABSTRACT

1,1,1,2-Tetrafluoroethane (R134a) is purified to remove 50–10,000 wt. ppm of 2-chloro-1,1-difluoroethylene (R1122) by contacting with a zeolite or carbon molecular sieve having an average pore diameter of 3.8 to 4.8 Angstroms. The zeolite or carbon molecular sieve is regenerated by inert gas stripping residual R134a, followed by a regeneration at elevated temperatures using an inert gas. Regeneration of the zeolite or carbon molecular sieve is accomplished without the substantial reduction in capacity for impurities.

20 Claims, No Drawings

REGENERATION OF ZEOLITES USED FOR PURIFYING 1,1,1,2-TETRAFLUOROETHANE

The invention relates generally to improvement of the process for making 1,1,1,2-tetrafluoroethane, $CH_2FCF_3$, designated also as refrigerant 134a (R134a). More particularly, the invention relates to purification of R134a by removing 2-chloro-1,1-difluoroethylene (R1122) by contacting with a zeolite, as disclosed in U.S. Pat. No. 4,906,796.

It has been found that when a precursor chlorofluorocarbon is reacted with hydrogen fluoride in the presence of a catalyst, R1122 is formed in small amounts. Because of its toxicity it must be removed from the product R134a.

An improved process for removing R1122 from R134a is disclosed in U.S. Pat. No. 4,906,796 which is incorporated herein by reference. Impurities are removed by adsorption on a zeolite having a mean pore size of about 3.8 to 4.8 Angstroms such as 5A synthetic zeolites and the natural zeolite, calcium chabazite. In order for the zeolites to be commercially useful, it is important that they be regenerable. However, since the zeolites can be damaged by exposure to HF, their capacity could be significantly reduced during regeneration of the zeolites. The present invention relates to the discovery of methods by which zeolites can be regenerated while avoiding the potential loss of adsorptive capacity.

SUMMARY OF THE INVENTION

In one embodiment, the invention is a method for regenerating zeolites, such as calcium chabazite, used for removing 2-chloro-1,1-difluoroethylene (R1122) from 1,1,1,2-tetrafluoroethane (R134a), comprising the following steps:

(a) removing R134a by stripping the zeolite with an inert gas at a temperature of about 0° to 60° C. and a pressure less than about 300 kPa, preferably less than about 100 kPa;

(b) separating and recovering R134a from the inert gas of (a);

(c) removing R1122 by passing an inert gas over said zeolite at a temperature of about 150° to 300° C. and a pressure less than about 300 kPa, preferably less than about 100 kPa.

In another aspect, the invention is a process for the purification of R134a by removing R1122 by contact with a zeolite, preferably calcium chabazite, wherein the improvement comprises regenerating said zeolite by a sequence of steps comprising:

(a) removing R134a by stripping the zeolite with an inert gas at a temperature of about 0. to 60° C and a pressure less than about 300 kPa, preferably less than about 100 kPa;

(b) separating from the inert gas stripped R134a of (a) and returning the separated R134a to the purification process;

(c) removing R1122 by passing an inert gas over said zeolite at a temperature of about 150° to 300° C. and a pressure of less than about 300 kPa, preferably less than about 100 kPa; and, (d) disposing of the R1122.

Examples of the inert gas employed in steps (a) and (c) above include nitrogen, argon, helium, carbon dioxide, or a low boiling fluorocarbon, such as R113. Air may also be used, although not preferred. The stripped R134a may be recovered by condensation from the stripping gas and recycled.

DESCRIPTION OF THE PREFERRED EMBODIMENTS

R134a Purification

U.S. Pat. No. 4,906,796 discusses a process wherein R134a containing only about 50-10,000 wt. ppm of R1122 is purified to remove substantially all of the R1122 with less than 10 wt. ppm remaining in the R134a. The R134a is passed over a sufficient amount of a zeolite having an average pore diameter of 3.8 to 4.8 Angstroms at a temperature of about −10° to 100° C., to remove substantially all of the R1122. Preferably, the zeolite is calcium chabazite or 5A synthetic zeolites. Alternatively, carbon molecular sieves having the same mean pore size could be used. Chabazite, a natural zeolite having the nominal formula $Ca_2Al_4Si_8O_{24}$ with elliptical pores of $3.7 \times 4.2$ Angstroms has been found to provide the best overall performance. It should be understood that since chabazite is a naturally derived material, it may contain minor amounts of impurities and related minerals with which it is found in nature. Alternatively, 5A synthetic zeolites having a mean pore size of about 4.3 Angstroms or carbon molecular sieves having similar pore size may be used.

The amount of the adsorbent will depend upon many factors, including the desired degree of removal of R-1122 and the on-stream time before regeneration is needed. The space velocity chosen will depend on a number of factors which will be familiar to those skilled in the art. The shape of the adsorbent bed may be affected by the temperature of operation since mass transfer considerations may become important at lower temperatures. The operating pressure will depend upon whether liquid or vapor contacting is desired and typically would be between about 100 to 1020 kPa.

Regeneration of Zeolites

The adsorbent will require regeneration in most instances. Otherwise, the purification of R134a by absorption would be prohibitively expensive, if the adsorbent required frequent replacement. Thus, it is important that the sorbent be regenerable and that loss in capacity for R1122 be minimized.

The most effective methods of regenerating zeolites will be discussed below. In general, it has been found that zeolites can be regenerated fully and returned to near-fresh condition by employing a multistep procedure. The same procedures may be employed with carbon molecular sieves.

When the impurities begin to break through the adsorbent bed after a period of use, it is necessary to regenerate the bed, usually while continuing to remove impurities with a second already-regenerated bed.

R134a should be removed from the zeolite prior to regeneration for removing the R1122. When R134a is present at regeneration temperatures, it is likely to degrade and the byproducts can be expected to have detrimental effects. In particular, hydrofluoric acid produced can attack the silica-alumina of the zeolite, changing its structure and reducing its capacity for impurities. This degradation of R134a also may lead to the deposition of carbon, resulting in a loss of capacity for R1122. Consequently, removal of residual R134a is an important first step in the regeneration of zeolites which have become saturated with impurities.

Since R134a and R1122 have similar boiling points, it might be anticipated that they would be removed together. If so, then recovery of the R134a stripped would be difficult since it would contain a higher concentration of impurities than the original feed-stream. I have found that it is possible to remove the R134a first and thereafter to strip off the R1122.

It has been found that regeneration of the zeolites or carbon molecular sieves which have been used to remove R1122 and R134a can be carried out in such a manner that the capacity of the adsorbent is fully recovered, even after many regenerations. This is, of course, essential for successful commercial practice since there would be significant losses of the R134a and R1122 if frequent replacement of the adsorbent were required. Also, the replacement of the adsorbent and disposal of the used material would present problems. In addition, the cost of replacing the adsorbent would be prohibitive.

In order to avoid the loss of the R134a and R1122 they should be purged from the adsorbent and the containment vessel to recover and conserve them. More importantly, the halogenated compounds must be removed in order to prevent a loss of capacity caused by deposit of decomposition products in the adsorbent pores or the attack of acids, particularly HF, on the adsorbent which could result in physical deterioration of the structure. Thus, substantially complete removal of the halogenated compounds is accomplished by purging the adsorbent with a flow of inert gas at an elevated temperature, either at atmospheric pressure or preferably under a vacuum. The temperature may be from about 0° C. to 60° C., preferably about 20° C. to 30° C. The operating pressure in the adsorbent bed during the purge step should be no more than about 300 kPa, preferably less than 100 kPa, and most preferably from about 22 kPa to 100 kPa.

The rate at which the gas passes through the adsorbent bed is adjusted to be at least 150 v/v-hr and at a maximum the rate which would cause an unacceptable pressure drop through the adsorbent. The gas itself should be inert with respect to the process, that is, gases typically considered inert would be included in the list of useful gases, but others not normally considered as inert could also be used provided that they have no seriously detrimental effect on the adsorbent or on the degree of regeneration. For example, air since it contains oxygen would not ordinarily be considered inert and it could cause the formation of undesirable peroxides, however, tests of air as a purge have shown that acceptable regeneration can be obtained. Its use would not be preferred but since it is the least expensive gas which could be considered it should be included in a list of possible inert gases. More conventional inert gases would be preferred, such as nitrogen, helium, argon, carbon dioxide and the like. Low boiling fluorocarbons such as R113, R114, R11, R12, and R13 may also be used. Purging of the halogenated compounds would be continued until essentially all of such materials have been removed, preferably until the effluent concentration in the sweep gas of halogenated compounds is less than about 5000 ppm. The halogenated compounds may be removed from the inert gas stream by cooling and condensation, after which the gas may be disposed of and the condensed materials recycled to the process for making R134a.

Once the bulk of the halogenated materials have been removed, the regeneration of the adsorbent is continued by passing a sweep gas over the adsorbent under more severe conditions to remove the residual adsorbed material, which is principally R1122. Clearly, the purge step must be capable of removing the residual R134a while leaving the R1122 on the adsorbent or else the regeneration would not serve to separate the two halogenated compounds. Thus, the inert gas will be passed over the adsorbent bed for at least 6 up to about 24 hours until substantially all of the R1122 remaining on the adsorbent has been removed. The temperature preferably will be maintained in the range of 150° C. to 225° C., depending upon whether the R1122 has been completely removed. After several cycles, it may be necessary to occasionally employ a higher temperature up to about 300° C. but higher temperatures are not preferred since they may lead to a loss of capacity due to deterioration of the adsorbent. The pressure used in the regeneration step may be the same as that used in the purge step but preferably will be lower. Generally, the pressure may be up to about 300 kPa, but preferably will be below 100 kPa, most preferably in the range of about 5 kPa to 100 kPa. There is an advantage for using atmospheric pressure for both the purge and regeneration steps since the equipment and operating costs will be lower and the risks associated with the infiltration of air into the equipment are eliminated. However, the regeneration is believed to be less effective when atmospheric pressure is used and thus for the most complete recovery of adsorbent capacity for R1122 purging and regeneration under vacuum conditions are recommended. Advantageously, the R1122 will be disposed of by being separated from the inert gas using condensation, absorption or other methods known to those skilled in the art and then returned to the process which produces R134a where R1,122 may be converted to a precursor to R134a. The R1122 could also be destroyed by burning or converted to another more useful compound.

Once the adsorbent has been regenerated, it should be cooled to the desired temperature for adsorption of R1122, that is about 25° C. and then placed into service. In commercial practice two or more beds of adsorbent typically would be used so that continuous operation is possible, while beds which have become saturated with R1122 are removed from service and regenerated.

EXAMPLE 1

Regeneration Using Vacuum and Sweep Gas

Impure R-134a containing 6500 ppm R-1122 was passed in liquid phase at 135 psig through a 229 mm long by 0.66 mm ID Inconel ™ column packed with 9.21 g of calcium chabazite (AW-500, supplied by UOP, crushed to 12-50 mesh and redried at 400° C.) at a flow rate of 0.6 g/min. Samples of the effluent from this column were taken periodically, and analyzed by gas chromatography using 20 a 3048 mm long×3.175 mm ID stainless steel column of 1% SP-1000 on 60/80 Carbopack B (purchased from Supelco Inc.) operated at 45° C. for 3 minutes, then programmed at 8° C./min to 200° C. The concentrations of R-1122 obtained from these analyses were plotted versus the weight of R-134a which had passed through the column, and the breakthrough (dynamic) capacity was calculated by noting the point at which the R-1122 concentration passed one half the feed concentration, and assuming that all of the R-1122 which had entered the column at that point was adsorbed.

After a period of time, the column was regenerated by (1) evacuating the column to a pressure of 22.66 kPa while passing nitrogen through the column at a rate of 38 mL/min for 1 hour, then (2) raising the temperature of the column to 170° C. for 17 hours, while lowering the applied pressure to 0.267 kPa, and maintaining the nitrogen flow rate at 38 mL/min. The column was cooled to room temperature, and reused for R-134a purification (on feed containing 4524 ppm R-1122). Table 1 below shows the effect on capacity of this regeneration procedure.

TABLE 1

| Run | Dynamic Capacity (mg R-1122/g) |
|---|---|
| Initial Run | 117.8 |
| After 1 regeneration | 103.8 |
| After 2 regenerations | 96.3 |
| After 3 regenerations | 87.0 |

EXAMPLE 2

Regeneration Using Sweep Gas but Without Vacuum

Impure R-134a containing 4552 ppm R-1122 was passed through a column of calcium chabazite and analyzed as in Example 1. The column was regenerated by (1) flushing the column at atmospheric pressure with nitrogen at 189 mL/min for 5 min to 1 hour, then (2) heating the column to 170° C. at atmospheric pressure for 17 hours while maintaining a nitrogen flow rate of 189 mL/min. The column was cooled to room temperature and reused for R-134a purification. Table 2 below shows the effect on capacity of this regeneration procedure.

TABLE 2

| Run | Feed Conc. (ppm) | Dynamic Capacity (mg R-1122/g) |
|---|---|---|
| Initial Run | 4552 | 88.4 |
| After 1st regeneration | 4552 | 75.4 |
| After 2nd regeneration | 9421 | 140.6* |
| After 3rd regeneration | 9421 | 85.0 |
| After 4th regeneration | 9421 | 98.3 |
| After 5th regeneration | 9421 | 100.2 |
| After 6th regeneration | 9421 | 115.8 |
| After 7th regeneration | 9421 | 134.4 |

*Dynamic capacity increase attributed to increased feed concentration.

EXAMPLE 3

Regeneration Using No Sweep Gas

Impure R-134a containing 6082 ppm R-1122 was passed through a column of calcium chabazite and analyzed as in Example 1. The column was regenerated by evacuating it to 24 kPa for 4 hours while heating it to 170° C. No sweep gas was used. The column was then cooled to room temperature and reused for R-134a purification. Table 3 below shows the effect on capacity of this regeneration procedure.

TABLE 3

| Run | Dynamic Capacity (mg R-1122/g) |
|---|---|
| Initial Run | >102.8 |
| After 1 regeneration | 71.2 |
| After 2 regenerations | 67.5 |
| After 3 regenerations | 30.3 |

It was concluded that using vacuum without the benefit of a sweep gas drastically reduced the dynamic capacity of the calcium chabazite.

EXAMPLE 4

Regeneration Using No Sweep Gas

Impure R-134a containing 6082 ppm R-1122 was passed through a column of calcium chabazite and analyzed as in Example 1. The column was regenerated by evacuating it to 0.27 kPa for 4 hours while heating it to 170° C. No sweep gas was used. The column was then cooled to room temperature and reused for R-134a purification. Table 4 below shows the effect on capacity of this regeneration procedure.

TABLE 4

| Run | Dynamic Capacity (mg R-1122/g) |
|---|---|
| Initial Run | 116.8 |
| After 1 regeneration | 66.8 |
| After 2 regenerations | 90.1 |

EXAMPLE 5

Regeneration Using No Sweep Gas or Temperature Increase

Impure R-134a containing 6082 ppm R-1122 was passed through a column of calcium chabazite and analyzed as in Example 1. The column was regenerated by evacuating it at room temperature to 0.267 kPa for 4-19 hours. No sweep gas was used. The column was then reused for R-134a purification. Table 5 below shows the effect on capacity of this regeneration procedure.

TABLE 5

| Run | Feed Conc. (ppm) | Regeneration Time (hours) | Dynamic Capacity (mg R-1122/g) |
|---|---|---|---|
| Initial Run | 6082 | — | >57.5 |
| After 1 regeneration | 6082 | 8 | 15.4 |
| After 2 regenerations | 4031 | 4 | 46.0 |
| After 3 regenerations | 4031 | 4 | 17.0 |
| After 4 regenerations | 4031 | 19 | 18.0 |

Again, it was concluded that a low vacuum without a sweep gas reduced the dynamic capacity drastically.

EXAMPLE 6

Regeneration Using R-113 as Sweep Gas

Impure R-134a containing 6019 ppm R-1122 was passed through a column of calcium chabazite and analyzed as in Example 1. The column was regenerated by (1) flushing the column at atmospheric pressure with R-113 flow rate of 40 mL/min for 1 hour, then (2) heating the column to 170° C. at atmospheric pressure for 8 hours while maintaining a R-113 flowrate of 40 mL/min. The column was cooled to room temperature and reused for R-134a purification. Table 6 below shows the effect on capacity of this regeneration procedure.

TABLE 6

| Run | Dynamic Capacity (mg R-1122/g) |
|---|---|
| Initial Run | >98.8 |
| After 1 regeneration | 93.8 |
| After 2 regenerations | 102.4 |
| After 3 regenerations | >88.0 |
| After 4 regenerations | >86.6 |

EXAMPLE 7

Regeneration Using Sweep Gas at Atmospheric Pressure

Impure R-134a containing 6019 ppm R-1122 was passed through a column of calcium chabazite and analyzed as in Example 1. The column was regenerated by (1) flushing the column at atmospheric pressure with nitrogen at 189 mL/min for 1 hour, then (2) heating the column to 300° C. at atmospheric pressure for 15 hours while maintaining a nitrogen flow rate of 189 mL/min. The column was cooled to room temperature and reused for R-134a purification. Table 7 below shows the effect on capacity of this regeneration procedure.

TABLE 7

| Run | Dynamic Capacity (mg R-1122/g) |
| --- | --- |
| Initial Run | 93.8 |
| After 1st regeneration | 101.6 |
| After 2 regenerations | 101.6 |
| After 3 regenerations | 97.3 |
| After 4 regenerations | 99.0 |
| After 5 regenerations | 99.0 |
| After 6 regenerations | 99.0 |

EXAMPLE 8

Regeneration Using Air as Sweep Gas

Impure R134a containing about 6000 ppm R1122 is passed through a column of calcium chabazite and analyzed as in Example 1. The column is regenerated by flushing the column at atmospheric pressure with air at 189 mL/min for 1 hour and then heating the column to 150° C. at atmospheric pressure for 15 hours while maintaining that air flow. After cooling to room temperature, the calcium chabazite has regained capacity for R1122.

I claim:

1. A method for regenerating zeolites or carbon molecular sieves used for removing 2-chloro-1,1-difluoroethylene (R1122) from 1,1,1,2-tetrafluoroethane (R134a) comprising:
   (a) removing R134a by stripping the zeolite or carbon molecular sieve with an inert gas at a temperature of about 0° to 60° C. and a pressure not higher than about 300 kPa;
   (b) separating and recovering R134a from the inert gas
   (c) removing R1122 from said zeolite by passing an inert gas over said zeolite or carbon molecular sieve at a temperature of about 150° to 300° C. and a pressure no higher than about 300 kPa.

2. The process of claim 1 wherein said inert gas of (a) is at least one member of the group consisting of nitrogen, argon, helium, carbon dioxide and low boiling fluorocarbons.

3. The process of claim 2 wherein said inert gas of (a) is nitrogen.

4. The process of claim 1 wherein said inert gas of (a) is air.

5. The process of claim 2 wherein said inert gas of (a) is R113.

6. The process of claim 1 wherein said inert gas of (c) is at least one member of the group consisting of nitrogen, argon, helium, carbon dioxide and low boiling fluorocarbons.

7. The process of claim 6 wherein said inert gas of (c) is nitrogen.

8. The process of claim 1 wherein said inert gas of (c) is air.

9. The process of claim 4 wherein said inert gas of (c) is R113.

10. The process of claim 1 wherein the pressure is no higher than about 100 kPa.

11. The process of claim 1 wherein said zeolite is calcium chabazite.

12. A process for purification of 1,1,1,2-tetrafluoroethane (R134a) by removing 2-chloro-1,1-difluoroethylene (R1122) by contacting said R134a with a zeolite or carbon molecular sieve wherein the improvement comprises regenerating said zeolite by a sequence of steps comprising:
   (a) removing R134a by stripping the zeolite or carbon molecular sieve with an inert gas at a temperature of 0° to 60° C. and a pressure of no higher than about 300 kPa;
   (b) separating from the inert gas of (a) the R-134a and returning the separated R134a to the purification process;
   (c) removing R1122 from said zeolite by passing an inert gas over said zeolite or carbon molecular sieve at a temperature of about 150° to 300° C. and a pressure of less than about 300 kPa; and,
   (d) disposing of the R1122.

13. The process of claim 12 wherein said inert gas of (a) is at least one member of the group consisting of nitrogen, argon, helium, carbon dioxide and low boiling fluorocarbons.

14. The process of claim 13 wherein said inert gas of (a) is nitrogen.

15. The process of claim 12 wherein said inert gas is air.

16. The process of claim 13 wherein said inert gas is R113.

17. The process of claim 12 wherein said inert gas of (c) is at least one member of the group consisting of nitrogen, argon, helium, carbon dioxide and low boiling fluorocarbons.

18. The process of claim 17 wherein said inert gas of (c) is nitrogen.

19. The process of claim 12 wherein said zeolite is calcium chabazite.

20. The process of claim 12 wherein the pressure is no higher than about 100 kPa.

* * * * *